(12) United States Patent
Biel et al.

(10) Patent No.: US 6,776,044 B2
(45) Date of Patent: Aug. 17, 2004

(54) ULTRASONIC DEVICE FOR INSPECTION

(75) Inventors: Roger Biel, Frankfurt am Main (DE); Martin Schubert, Leipzig (DE); Wolfgang Grill, Königstein i.Ts. (DE)

(73) Assignee: Novartis AG, Basel (SE)

( * ) Notice: Subject to any disclaimer, the term of this patent is extended or adjusted under 35 U.S.C. 154(b) by 16 days.

(21) Appl. No.: 10/047,042

(22) Filed: Oct. 22, 2001

(65) Prior Publication Data

US 2002/0149744 A1 Oct. 17, 2002

(30) Foreign Application Priority Data

Oct. 23, 2000 (EP) .............................. 00122985

(51) Int. Cl.[7] .............................................. G01N 29/04
(52) U.S. Cl. ....................... 73/595; 73/596; 134/901
(58) Field of Search ...................... 73/585, 596, 632, 73/644; 134/901

(56) References Cited

U.S. PATENT DOCUMENTS

| | | | |
|---|---|---|---|
| 3,973,760 A | * | 8/1976 | Browning et al. .......... 134/901 |
| 4,035,082 A | | 7/1977 | Kirschen ................... 356/114 |
| 5,585,563 A | * | 12/1996 | Bui ............................ 73/644 |

FOREIGN PATENT DOCUMENTS

| | | |
|---|---|---|
| EP | 0 357 905 | 3/1990 |
| EP | 0 491 663 | 6/1992 |

OTHER PUBLICATIONS

Dr. Hielscher GMBH: "UIP 250 Industrial Ultrasonic Processor 250 W" [online]Nov. 12, 2000 [retrieved on Mar. 6, 2001].

* cited by examiner

*Primary Examiner*—John E. Chapman
(74) *Attorney, Agent, or Firm*—Jian S. Zhou; Robert Gorman; R. Scott Meece

(57) ABSTRACT

The invention is based on the problem of providing an inspection device and an inspection method, which recognise the defective lenses, which are difficult to detect with conventional optical methods, with a high degree of reliability. According to the invention, the contact lenses are exposed to an ultrasonic field, which leads to destruction of defective lenses, while perfect lenses are as a rule not destroyed. In particular, the method is capable of detecting cracks which are often overlooked by optical methods, since this type of defect reacts especially sensitively to the soundwaves being received.

24 Claims, 1 Drawing Sheet

ULTRASONIC DEVICE FOR INSPECTION

BACKGROUND OF THE INVENTION

The invention relates to a device and a method for the automatic inspection of ophthalmic lenses, especially contact lenses, in an automatic lens manufacturing process.

SUMMARY OF INVENTION

The production of contact lenses using conventional methods, such as rotary processes for hard contact lenses and pouring processes for soft contact lenses in disposable plastic moulds is relatively expensive. As a rule, these contact lenses are used for a period of one year to one month. However, technical advancement in recent years has enabled contact lenses to be produced, which are worn only on one day and are replaced afterwards by new contact lenses. However, this has been made possible only through a high degree of automation of the production plants. Production of these contact lenses advantageously takes place using reusable mould halves, the matrix and the patrix, which normally consist of glass or quartz. Between these mould halves is a hollow cavity, which corresponds to the subsequent contact lens shape. Before closing the mould halves, a polymer solution is measured into the matrix. The upper mould half is exposed to UV light, which leads to crosslinking of the lens material. Subsequently, the lens is removed from the mould half with suction grips and is placed in the pack.

In order to assure constant quality of the contact lenses, provisions are in place for automatic inspection of the contact lenses using industrial image-processing methods. In image-processing, the lenses are tested both in the mould halves and at the vacuum grips. An image processing method of this kind is described for example in EP patent 491 663. Moreover, using optical methods, not all defects of contact lenses can be detected without problems, so that defective contact lenses pass the quality control as defect-free and it is only the customer who establishes the defects when he removes the lens from the pack or even when he first wears the contact lens.

The invention is based on the problem of providing an inspection device and an inspection method, which recognise the defective lenses, which are difficult to detect with conventional optical methods, with a high degree of reliability.

According to the invention, the contact lenses are exposed to an ultrasonic field, which leads to destruction of defective lenses, while perfect lenses are as a rule not destroyed. In particular, the method is capable of detecting cracks in contact lenses which are often overlooked by optical methods, since this type of defect reacts especially sensitively to the soundwaves being received.

Further details and advantages of the invention may be seen from the description that follows and the drawing. In the drawing,

DETAILED DESCRIPTION OF THE PREFERRED EMBODIMENTS

Figure 1:
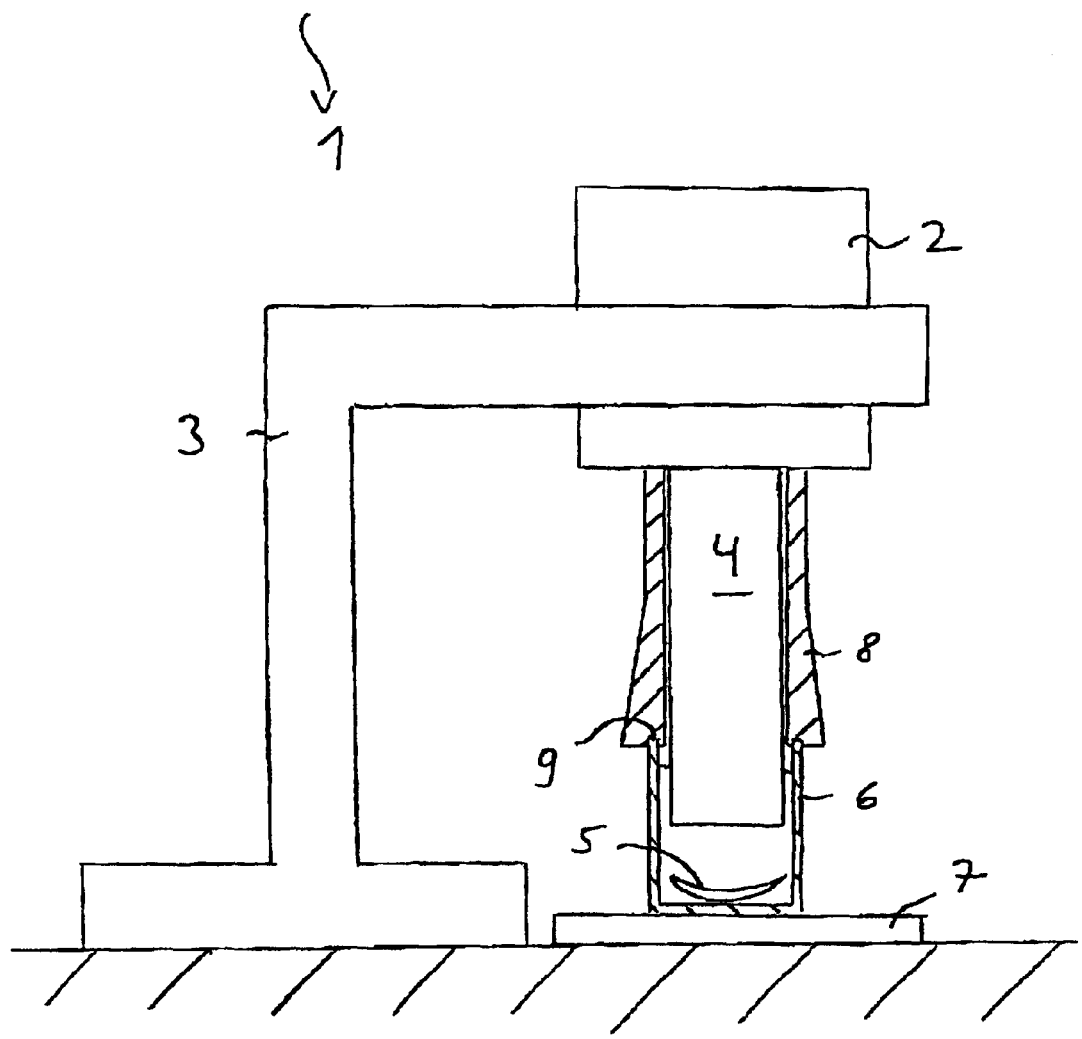
FIG. 1 shows a schematic illustration of an inspection device according to the invention.

The inspection device 1 illustrated schematically in FIG. 1 consists of an ultrasonic processor 2, which is preferably fixed by a holder 3. The ultrasonic processor 2 has a rod-shaped sonotrode 4, which emits the ultrasonic waves. The ultrasonic processor 2 is preferably a UIP 250 appliance from Hielscher. The operating frequency of this device is from about 20 to 30 kHz, preferably about 24 kHz ±1 kHz. It is, however, also conceivable to use other frequency ranges. The ultrasonic intensity is from about 80 to 150 $W/cm^2$, preferably about 138 $W/cm^2$ and the maximum amplitude is in the region of ca. 250 $\mu m$. The butt end of the sonotrode 4 has a diameter of 14 mm. However, it is within the scope of the invention to use other devices with other parameters.

To examine a contact lens 5 with the ultrasonic processor 2, the contact lens 5 is inserted into a holding container. This container is preferably a glass cuvette 6 of a basic cylindrical shape. The cuvette 6 is preferably filled with water or a comparable test liquid. The cuvette 6 is advantageously located on a spring-loaded holding plate 7. The positioning of the contact lens 5 in the cuvette 6 is of no importance to the examination process. After inserting the contact lens in the cuvette 6, the sonotrode 4 is plunged into the container 6, whereby the sonotrode 4 is immersed so deeply that the bottom is surrounded by water and thus the oscillations emanating from the sonotrode 4 are transferred to the water. The sonotrode 4 is suitably surrounded by a sealing sleeve 8, which is advantageously tuned to the vibration behaviour of the sonotrode 4. The sealing sleeve 8 is preferably made of Teflon and is pushed over the sonotrode 4 and held by a sealing ring at the oscillation node of the sonotrode 4. At the end facing the cuvette 6, the sealing sleeve 8 preferably has a groove or recess 9 to cover the edge of the glass cuvette 6, so that no liquid can escape from the container 6. The sonotrode 4 is immersed into the container 6 to such an extent that the sealing sleeve 8 rests on the edge of the glass cuvette. In this way, a defined depth is given. By expelling the water, it can be ensured that no air remains in the container 6 and the ultrasound is ideally coupled in. The distance from the sonotrode 4 to the glass bottom of the cuvette 6, which is provided for the contact lens, is advantageously about 9 mm. After immersing the sonotrode 4 into the cuvette 6, the ultrasonic processor 2 is switched on and the contact lens 5 in the cuvette 6 is sonicated.

Using the device according to the invention, examinations were made of perfect and defective lenses, the quality of the lenses having already been examined using a shadowgraph.

The power and duration parameters of sonication are of crucial importance to the results of the examination. If too high power is applied, almost all the originally perfect lenses are destroyed by the ultrasonic treatment, and if the power is too low, defective lenses are also not destroyed. The same applies to the time during which the lens is exposed to sonication. By varying the time or the power, the energy applied overall is modified. The range regarded as acceptable for the examinations is 5–15% destruction of all lenses rated to be perfect. Since the lenses have been graded as perfect using an optical examination method, it is quite possible that the lenses have defects which can only be detected mechanically. For the ultrasonic processor used, a duration of 6 seconds and 70% of the maximum power of the device proved to be the optimum values. However, within the context of the invention, other settings for the duration and intensity of sonication may also be chosen. In particular, when choosing another ultrasonic processor, it may be expedient to modify the parameters.

The examinations for defective lenses are suitably carried out using the above-mentioned setting. The examination results show that lenses especially with cracks were destroyed by almost 100%. For other types of defect, the destruction rate was not so high. The examination method is thus particularly suitable for detecting defective lenses with cracks.

What we claim is:

1. An inspection device for inspecting an ophthalmic lens for defects, comprising: an ultrasonic processor; a holding container open at the top and filled with a test liquid at a level sufficient high so that, one or more ophthalmic lenses to be inspected are surrounded entirely by the test liquid in the holding container; and a sonotrode immersed in the test liquid for creating a sufficiently high and homogeneous ultrasonic field capable of destroying only defective lenses located in the holding container.

2. An inspection device according to claim 1, wherein the ultrasonic field has a power intensity of 80–150 $W/cm^2$.

3. An inspection device according to claim 2, wherein the ultrasonic field has a frequency of from 20 to 30 kHz.

4. An inspection device according to claim 2, wherein the ultrasonic field has a frequency of from 23 to 25 kHz.

5. An inspection device according to claim 1, wherein the holding container is of cylindrical shape.

6. An inspection device according to claim 1, wherein the ultrasonic field has a frequency of from 20 to 30 kHz.

7. An inspection device according to claim 1, wherein the ultrasonic field has a frequency of from 23 to 25 kHz.

8. An inspection device according to claim 1, wherein the butt end of the sonotrode has a diameter of 14 mm.

9. An inspection device according to claim 1, wherein the holding container is mounted on a spring-loaded holding plate.

10. An inspection device according to claim 1, wherein the sonotrode is surrounded by a sealing sleeve which seals off the holding container during immersion of the sonotrode.

11. An inspection device according to claim 1, wherein the ophthalmic lenses are contact lenses.

12. An inspection device of claim 1, wherein the ultrasonic field has a power intensity of 136–140 $W/cm^2$.

13. A method of inspecting ophthalmic lenses for defects, comprising the steps of: placing the ophthalmic lenses in a holding container filled with a test liquid in such a way that the test liquid surrounds entirely the ophthalmic lenses; and exposing the ophthalmic lenses to an ultrasonic field thereby leading to destruction of defective lenses.

14. A method according to claim 13, wherein the power intensity of the ultrasonic field lies in the range of 80 to 150 $W/cm^2$.

15. A method of claim 14, wherein the power intensity of the ultrasonic field is 138 $W/cm^2$.

16. A method of claim 14, wherein an ultrasonic processor with a sonotrode is used to produce the ultrasonic field.

17. A method according to claim 13, wherein an ultrasonic processor with a sonotrode is used to produce the ultrasonic field.

18. A method according to claim 17, wherein a sonotrode with a butt end of 14 mm diameter is used.

19. A method according to claim 17, wherein the sonotrode is surrounded by a sealing sleeve which seals off the holding container during immersion of the sonotrode.

20. A method according to claim 13, wherein a cylindrical holding container is used to position the ophthalmic lenses in the test liquid.

21. A method according to claim 13, wherein the frequency range is from 20 to 30 kHz.

22. A method according to claim 21, wherein the frequency range is from 23 to 25 kHz.

23. A method according to claim 13, wherein ophthalmic lenses are soft contact lenses.

24. A method of claim 13, wherein the ophthalmic lenses are contact lenses.

* * * * *